United States Patent
Lesniak et al.

(10) Patent No.: US 11,969,496 B2
(45) Date of Patent: *Apr. 30, 2024

(54) NON-GREASY PERSONAL CARE COMPOSITIONS

(71) Applicant: Colgate-Palmolive Company, New York, NY (US)

(72) Inventors: Ewelina Lesniak, Linden, NJ (US); Kathy Potechin, Short Hills, NJ (US); Lauren Decina, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/874,412

(22) Filed: Jul. 27, 2022

(65) Prior Publication Data

US 2022/0362135 A1    Nov. 17, 2022

Related U.S. Application Data

(60) Continuation of application No. 16/590,681, filed on Oct. 2, 2019, now Pat. No. 11,433,018, which is a division of application No. 15/512,602, filed as application No. PCT/US2015/036498 on Jun. 18, 2015, now Pat. No. 10,470,999, which is a continuation of application No. PCT/US2014/056888, filed on Sep. 23, 2014.

(51) Int. Cl.
| | | |
|---|---|---|
| *A61K 8/92* | (2006.01) | |
| *A61K 8/02* | (2006.01) | |
| *A61K 8/27* | (2006.01) | |
| *A61K 8/34* | (2006.01) | |
| *A61K 8/37* | (2006.01) | |
| *A61K 8/9789* | (2017.01) | |
| *A61Q 17/04* | (2006.01) | |
| *A61Q 19/00* | (2006.01) | |

(52) U.S. Cl.
CPC ............ *A61K 8/927* (2013.01); *A61K 8/0229* (2013.01); *A61K 8/27* (2013.01); *A61K 8/34* (2013.01); *A61K 8/342* (2013.01); *A61K 8/37* (2013.01); *A61K 8/92* (2013.01); *A61K 8/922* (2013.01); *A61K 8/9789* (2017.08); *A61Q 17/04* (2013.01); *A61Q 19/00* (2013.01); *A61K 2800/31* (2013.01)

(58) Field of Classification Search
None
See application file for complete search history.

(56) References Cited

U.S. PATENT DOCUMENTS

| | | |
|---|---|---|
| 5,667,770 A | 9/1997 | Szweda et al. |
| 6,290,940 B1 | 9/2001 | Meyers et al. |
| 6,503,944 B1 | 1/2003 | Chanchani |
| 6,585,985 B2 | 7/2003 | Sakuta |
| 7,009,064 B2 | 3/2006 | Osorio et al. |
| 7,309,496 B2 | 12/2007 | Johansson et al. |
| 7,547,211 B2 | 6/2009 | Swanick |
| 7,772,181 B2 | 8/2010 | Amin et al. |
| 7,803,902 B2 | 9/2010 | Amin et al. |
| 8,802,118 B2 | 8/2014 | Ilekti et al. |
| 8,945,516 B2 | 2/2015 | Tamarkin et al. |
| 10,470,998 B2 * | 11/2019 | Lesniak ............. A61K 8/927 |
| 10,470,999 B2 * | 11/2019 | Lesniak ............. A61K 8/342 |
| 11,433,018 B2 * | 9/2022 | Lesniak ............. A61K 8/92 |
| 2005/0002973 A1 | 1/2005 | Johansson et al. |
| 2010/0015074 A1 * | 1/2010 | Blin ................. A61K 8/375 |
| | | 424/63 |
| 2010/0015082 A1 | 1/2010 | Ting-Jenulis et al. |
| 2011/0256075 A1 | 10/2011 | Oliveira Dias et al. |
| 2012/0225106 A1 | 9/2012 | Ross et al. |
| 2012/0237466 A1 | 9/2012 | Graham |

FOREIGN PATENT DOCUMENTS

| | | |
|---|---|---|
| JP | H11-228332 | 8/1999 |
| WO | 2007/007287 | 1/2007 |
| WO | 2007/133720 | 11/2007 |
| WO | 2008/038147 | 4/2008 |
| WO | 2010/109409 | 9/2010 |
| WO | 2011/039637 | 4/2011 |
| WO | 2011/039638 | 4/2011 |
| WO | 2012/158627 | 11/2012 |

OTHER PUBLICATIONS

Clean & Company, 2009, "Mrs. Meyer's Clean Day Baby Diaper Balm," Mintel GNPD AN: 1111377.
Food and Drug Administration, 2011, "Labeling and Effectiveness Testing; Sunscreen Drug Products for Over-the-Counter Human Use," Federal Register Rule https://www.govinfo.gov/content/pkg/FR-2011-06-17/pdf/2011-14766.pdf [FR Doc. 2011-14766 Filed Jun. 16, 2011; Publication Date Jun. 17, 2011] RIN 0910-AF43.
International Search Report and Written Opinion in International Application No. PCT/US2014/056888, dated Jun. 9, 2015.

(Continued)

*Primary Examiner* — Dominic Lazaro

(57) ABSTRACT

An anhydrous personal care composition, comprising: (a) 45 to 60 weight % of at least one ester, selected from (i) triglycerides, (ii) diglycerides, (iii) monoglycerides, (iv) monoesters of diols, and (v) diesters of diols; (b) a first wax having a melting point of from 35° C. to 72° C. present in an amount of 5 to 25 weight %; (c) a second wax having a melting point of 73 to 90° C. present in an amount of 0.5 to 15 weight %; and (d) at least one plant oil having a saponification value of from 150 to 275 mg KOH/g present in an amount of 5 to 35 weight.

20 Claims, No Drawings

(56) References Cited

OTHER PUBLICATIONS

International Search Report and Written Opinion in International Application No. PCT/US2015/036498, dated Oct. 9, 2015.
Kiko, 2013, "Kiko After Sun SOS Stick," Mintel GNPD AN: 2104389.
Laverana, 2011, "Lavera Naturkosmetik Sun Sensitiv," Mintel GNPD AN: 1624210.
Pure Altitude, 2014, "Baume des Montagnes SOS Repair Repairing Face & Body Balm," Mintel GNPD AN: 2253486.

* cited by examiner

NON-GREASY PERSONAL CARE COMPOSITIONS

CROSS REFERENCE TO RELATED APPLICATIONS

This application is a continuation of U.S. application Ser. No. 16/590,681, filed on Oct. 2, 2019, which is a divisional of U.S. application Ser. No. 15/512,602, filed on Mar. 20, 2017, which is a U.S. national stage application under 35 U.S.C. § 371 of PCT Application No. PCT/US2015/036498, filed on Jun. 18, 2015, which claims priority to PCT Application No. PCT/US2014/056888, filed on Sep. 23, 2014, the entire contents of each of which are incorporated herein by reference.

BACKGROUND

Various natural personal care compositions (i.e. personal care compositions which are formed from natural ingredients) have been shown to lack robustness against microbial attack. In order to address this issue, anhydrous products have been developed. As these products are anhydrous, they do not support microbial growth and are therefore micro-robust. However, anhydrous base formulations (which contain mainly oils and waxes) tend to be very greasy and to have a "heavy" skin feel, which some consumers find to be undesirable. In the case of anhydrous compositions which contain certain metal oxides, e.g. zinc oxide or titanium oxide, the compositions can also leave a white residue on the skin following application. Again, some consumers also find this "whitening" effect to be undesirable. It would therefore be desirable to provide a natural personal care composition which is micro-robust and which is non-greasy. It would also be desirable to provide such a composition which does not leave a white residue on the skin following application. It would also be desirable for such compositions to be physically stable at high and low temperatures.

BRIEF SUMMARY

In one aspect, an anhydrous personal care composition, comprising: (a) at least one ester, wherein said at least one ester is selected from one or more of the following groups: (i) triglycerides, (ii) diglycerides, (iii) monoglycerides, (iv) monoesters of diols, and (v) diesters of diols, and wherein a total concentration of said at least one ester is 45 to 60 weight %, based on the total weight of the composition; (b) a first wax having a melting point of 35° C. to 72° C. present in an amount of 5 to 25 weight %, based on the total weight of the composition; (c) a second wax having a melting point of 73° C. to 90° C. present in an amount of 0.5 to 15 weight % based on the total weight of the composition; (d) at least one plant oil having a saponification value of 150 to 275 mg KOH/g, wherein a total concentration of said at least one plant oil is from 5 to 35 weight %, based on the total weight of the composition.

For avoidance of doubt, elements (a), (b), (c), and (d) in the foregoing formulation are separate components which are combined to provide the composition described. For example, the "at least one ester" would not be considered part of the plant oil or the waxes, any ester that is part of the waxes or plant oils would not be considered part of the "at least one ester", and any wax that is part of the plant oil would not be considered part of the waxes of elements (b) or (c).

As conventionally defined, waxes are solid at room temperature, e.g., having a melting point between 35° C. and 90° C. In some embodiments, the waxes may be selected from, for example, (i) monoesters of long chain fatty acids and long chain fatty alcohols, (ii) triglycerides of saturated fatty acids; and (iii) mixtures thereof.

Plant oils are typically liquid at room temperature, e.g. having a melting point between −25° C. and 30° C.

Optionally, the first wax comprises at least one wax chosen from beeswax, candelilla wax, bayberry wax, and combinations thereof.

Optionally, the second wax comprises at least one wax chosen from hydrogenated castor oil, sunflower wax, sunflower seed wax, carnauba wax, rice bran wax, and combinations thereof.

Optionally, the first wax is present in an amount of 8 to 18 weight % based on the total weight of the composition, optionally 11 to 15 weight %.

Optionally, the second wax is present in an amount of weight 0.5 to 10 weight % based on the total weight of the composition, optionally 0.5 to 5 weight % or 1 to 3 weight %.

Optionally, the first wax has a melting point of 38° C. to 65° C., optionally 45° C. to 65° C. or 60° C. to 65° C.

Optionally, the second wax has a melting point of 78° C. to 85° C., optionally 77° C. to 83° C.

Optionally, the first wax is beeswax and the second wax is hydrogenated castor oil.

Optionally, the hydrogenated castor oil has a melting point of 77° C. to 83° C., optionally 80° C.

Optionally, the total concentration of the at least one ester is from 50 to 55 weight %, based on the total weight of the composition.

Optionally, the at least one ester is selected from: monoglycerides of capric acid; monoglycerides of caprylic acid; capric triglyceride; caprylic triglyceride; stearic triglyceride; monoesters of ethylene glycol and stearic acid; acetylated glycol stearate; glyceryl dilaurate; propylene glycol dicaprate; 1,3-propanediol dicaprylate; PEG-6 caprylic/capric glycerides; cocoglycerides; and combinations thereof.

Optionally, the at least one ester is a combination of caprylic triglyceride and capric triglyceride, Optionally, a weight ratio of caprylic triglyceride to capric triglyceride is from 70:30 to 50:50, optionally about 60:40.

Optionally, the total concentration of the at least one plant oil is from 5 to 30 weight %, based on the total weight of the composition.

Optionally, the total concentration of the at least one plant oil is from 8 to 30 weight %, based on the total weight of the composition.

Optionally, the total concentration of the at least one plant oil is from 10 to 21 weight %, based on the total weight of the composition.

Optionally, the at least one plant oil comprises at least one plant oil chosen from sunflower oil, high oleic sunflower oil, coconut oil, palm oil, sweet almond oil, castor oil, canola oil, soybean oil, avocado oil, olive oil, acai oil, andiroba oil, apricot kernel oil, argan oil, passion fruit oil, manila oil, mango oil, shea oil, macadamia nut oil, brazil nut oil, borage oil, copaiba oil, grape seed oil, buriti oil, sesame oil, flaxseed oil, blueberry oil, cranberry oil, blackberry oil, plum oil, raspberry oil, babassu oil, camelina oil, camellia oil, walnut oil, wheat germ oil, calendula oil, cherry kernel oil, cucumber seed oil, papaya oil, aloe vera oil, hemp oil, safflower oil, or a combination of any two or more thereof.

Optionally, the at least one plant oil comprises at least one oil chosen from sunflower oil, high oleic sunflower oil, coconut oil, hemp oil, avocado oil, olive oil, sesame oil, shea oil, safflower oil, argan oil, raspberry oil, or a combination of any two or more thereof.

Optionally, the at least one plant oil has a melting point of −25° C. to 30° C.

Optionally, the at least one plant oil comprises a plant oil which has a saponification value of 150 to 200 mg KOH/g.

Optionally, the at least one plant oil is a plant oil which has a saponification value of 170 to 200 mg KOH/g.

Optionally, the plant oil is sunflower oil, optionally high oleic sunflower oil.

Optionally, the at least one plant oil is a combination of a first oil and a second oil, the first oil having a saponification value of 150 to 200 mg KOH/g and the second oil having a saponification value of 220 to 275 mg KOH/g.

Optionally, the first oil is present at a concentration of 10 to 20 weight %, based on the total weight of the composition, and the second oil is present at a concentration of 1 to 10 weight %, based on the total weight of the composition.

Optionally, the first oil is present at a concentration of 12 to 14 weight %, based on the total weight of the composition, and the second oil is present at a concentration of 3 to 7 weight %, based on the total weight of the composition.

Optionally, the first oil has a melting point of −18° C. to −5° C. and the second oil has a melting point of 10° C. to 25° C.

Optionally, the first oil is sunflower oil and the second oil is coconut oil.

Optionally, the composition further comprises a vegetable fat having a melting point of 31° C. to 60° C.

Optionally, the vegetable fat is at least one material chosen from cocoa butter, shea butter, palm butter, tucuma butter, avocado butter, kokum butter, olive butter, shorea butter, manoi butter, coffee butter, soy butter, jojoba butter, cupuacu butter, mango butter, pistachio butter, pumpkin seed butter, brazil nut butter, hemp seed butter, illipe butter, murumuru butter, ucuuba butter, and combinations thereof.

Optionally, the vegetable fat is present in a concentration of 1 to 10 weight %, based on the total weight of the composition.

Optionally, the composition further comprises zinc oxide.

Optionally, the zinc oxide is present in a concentration of 10 to 30 weight %, based on the total weight of the composition.

Optionally, the composition comprises (i) 50 to 60 weight % of a combination of caprylic triglyceride and capric triglyceride, wherein the weight ratio of caprylic triglyceride to capric triglyceride is about 60:40; (ii) 13.5 to 15 weight % beeswax; (iii) 1 to 3 weight % hydrogenated castor oil; (iv) 10 to 12.5 weight % sunflower oil; and (v) 10 to 22 weight % zinc oxide.

Optionally, the composition is one of:
20 weight % zinc oxide, 10 weight % sunflower oil, 53 weight % caprylic/capric triglyceride, 15 weight % beeswax, and 2 weight % hydrogenated castor oil;
20 weight % zinc oxide, 12.5 weight % sunflower oil, 52 weight % caprylic/capric triglyceride, 13.5 weight % beeswax, and 2 weight % hydrogenated castor oil;
20 weight % zinc oxide, 12.1 weight % sunflower oil, 52 weight % caprylic/capric triglyceride, 13.5 weight % beeswax, 2 weight % hydrogenated castor oil, and 0.4 weight % fragrance;
12 weight % zinc oxide, 12.5 weight % sunflower oil, 60 weight % caprylic/capric triglyceride, 13.5 weight % beeswax, and 2 weight % hydrogenated castor oil;
12 weight % zinc oxide, 12.5 weight % sunflower oil, 55 weight % caprylic/capric triglyceride, 13.5 weight % beeswax, 5 weight % shea butter, and 2 weight % hydrogenated castor oil;
12 weight % zinc oxide, 12.5 weight % sunflower oil, 55 weight % caprylic/capric triglyceride, 13.5 weight % beeswax, 5 weight % coconut oil, and 2 weight % hydrogenated castor oil;
12 weight % zinc oxide, 12.5 weight % sunflower oil, 60 weight % caprylic/capric triglyceride, 13.5 weight % beeswax, and 2 weight % hydrogenated castor oil;
12 weight % zinc oxide, 12.5 weight % sunflower oil, 52 weight % caprylic/capric triglyceride, 13.5 weight % beeswax, 5 weight % coconut oil, 3 weight % shea butter, and 2 weight % hydrogenated castor oil;
the composition comprises or consists of 20 weight % zinc oxide, 10.4 weight % sunflower oil, 48% caprylic/capric triglyceride, 13.5% beeswax, 5 weight % sunflower seed wax, 3 weight % hydrogenated castor oil, and 0.1 weight % oil; or
20 weight % zinc oxide, 7.4 weight % sunflower oil, 51% caprylic/capric triglyceride, 13.5% beeswax, 5 weight % sunflower seed wax, 3 weight % hydrogenated castor oil, and 0.1 weight % oil.

Optionally, the composition is a stick.

Optionally, the composition is not an antiperspirant or a lip balm.

Optionally, the composition is a sunscreen or a diaper cream.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Unless otherwise specified, all experiments described herein are conducted at 25° C. and at atmospheric pressure.

As used herein, the term "anhydrous composition" indicates that the composition contains 2 weight % or less free water. In other embodiments, the maximum amount of water is 1.5 weight %, 1 weight %, or 0.5 weight %. In certain embodiments, there is no free water. When calculating the water content, water molecules that are part of a hydrate of a material are not counted.

As used herein, the term "natural composition" indicates that the composition is formulated from ingredients which are extracted from the earth or sea, derived from plants, or synthesized by other organisms. Similarly, the term "natural ingredients" as used herein indicates ingredients which are extracted from the earth or sea, derived from plants, or synthesized by other organisms.

As used herein, the "saponification value" (SAP value) of an oil is the number of milligrams (mg) of potassium hydroxide (KOH) which is required to saponify 1 g of the oil.

As discussed above, personal care compositions formulated from natural ingredients may be formulated so as to be anhydrous in order to ensure micro-robustness in the package and during consumer use. However, such anhydrous compositions have previously been found to have a heavy and greasy feel, which some consumers find undesirable. It would therefore be desirable to provide a natural personal care composition which is micro-robust and which is non-greasy.

Anhydrous compositions which contain certain metal oxides, e.g. zinc oxide or titanium oxide, can leave a white residue on the skin following application. Consumers may also find this "whitening" effect to be undesirable. It would therefore be desirable to provide a natural personal care composition which is micro-robust and non-greasy, and in which the amount of white residue left on the skin following application is minimized.

It would also be desirable to provide a natural personal care composition which is micro-robust and non-greasy, and which does not leave a white residue on the skin following application, which is also physically stable at high and low temperatures (e.g. which does not exhibit separation into a bulk solid phase and a bulk liquid phase at high and low temperatures). It would also be desirable to formulate such compositions from all-natural ingredients (i.e. "100% natural" compositions).

Therefore, in one aspect, there is provided an anhydrous personal care composition, comprising: (a) at least one ester, wherein said at least one ester is selected from one or more of the following groups: (i) triglycerides, (ii) diglycerides, (iii) monoglycerides, (iv) monoesters of diols, and (v) diesters of diols, and wherein a total concentration of said at least one ester is 45 to 60 weight %, based on the total weight of the composition; (b) a first wax having a melting point of 35° C. to 72° C. present in an amount of 5 to 25 weight %, based on the total weight of the composition; (c) a second wax having a melting point of 73° C. to 90° C. present in an amount of 0.5 to 15 weight % based on the total weight of the composition; (d) at least one plant oil having a saponification value of 150 to 275 mg KOH/g, wherein a total concentration of said at least one plant oil is from 5 to 35 weight %, based on the total weight of the composition.

The present inventors have surprisingly found that, in addition to having good micro-robustness, such compositions have reduced greasiness and an improved after-feel (such as reduced tackiness and drag) on the skin as compared to other anhydrous compositions. Such compositions are also physically stable at high and low temperatures.

The present inventors have also surprisingly found that the amount of white residue remaining on the skin following application of the composition is reduced when the compositions comprise a first wax having a melting point of 35° C. to 72° C., and a second wax having melting point of 73° C. to 90° C.

The present inventors have also surprisingly found that such compositions are also physically stable (i.e. do not exhibit separation into a bulk solid portion and a bulk liquid portion) when stored at 49° C./0% relative humidity for a period of 13 weeks, and when stored at 40° C./75% relative humidity for a period of 13 weeks, and show acceptable dispensing characteristics in addition to being non-greasy.

In certain embodiments, the first wax comprises at least one wax chosen from beeswax, candelilla wax, bayberry wax, and combinations thereof.

In certain embodiments, the second wax comprises at least one wax chosen from hydrogenated castor oil, sunflower wax, sunflower seed wax, carnauba wax, rice bran wax, and combinations thereof.

In certain embodiments, the first wax is present in an amount of 8 to 18 weight % based on the total weight of the composition, optionally 11 to 15 weight %.

In certain embodiments, the second wax is present in an amount of weight 0.5 to 10 weight % based on the total weight of the composition, optionally 0.5 to 5 weight % or 1 to 3 weight %.

In certain embodiments, the first wax has a melting point of 38° C. to 65° C., optionally 45° C. to 65° C. or 60° C. to 65° C.

In certain embodiments, the second wax has a melting point of 78° C. to 85° C., optionally 77° C. to 83° C.

In certain embodiments, the first wax is beeswax and the second wax is hydrogenated castor oil.

In certain embodiments, the hydrogenated castor oil has a melting point of 77° C. to 83° C., optionally 80° C.

In certain embodiments, the total concentration of the at least one ester is from 50 to 55 weight %, based on the total weight of the composition.

In certain embodiments, the at least one ester is selected from: monoglycerides of capric acid; monoglycerides of caprylic acid; capric triglyceride; caprylic triglyceride; stearic triglyceride; monoesters of ethylene glycol and stearic acid; acetylated glycol stearate; glyceryl dilaurate; propylene glycol dicaprate; 1,3-propanediol dicaprylate; PEG-6 caprylic/capric glycerides; cocoglycerides; and combinations thereof.

In certain embodiments, the at least one ester is a combination of caprylic triglyceride and capric triglyceride, In certain embodiments, a weight ratio of caprylic triglyceride to capric triglyceride is from 70:30 to 50:50, optionally about 60:40.

In certain embodiments, the total concentration of the at least one plant oil is from 5 to 30 weight %, based on the total weight of the composition.

In certain embodiments, the total concentration of the at least one plant oil is from 8 to 30 weight %, based on the total weight of the composition.

In certain embodiments, the total concentration of the at least one plant oil is from 10 to 21 weight %, based on the total weight of the composition.

In certain embodiments, the at least one plant oil comprises at least one plant oil chosen from sunflower oil, high oleic sunflower oil, coconut oil, palm oil, sweet almond oil, castor oil, canola oil, soybean oil, avocado oil, olive oil, acai oil, andiroba oil, apricot kernel oil, argan oil, passion fruit oil, manila oil, mango oil, shea oil, macadamia nut oil, brazil nut oil, borage oil, copaiba oil, grape seed oil, buriti oil, sesame oil, flaxseed oil, blueberry oil, cranberry oil, blackberry oil, plum oil, raspberry oil, babassu oil, camelina oil, camellia oil, walnut oil, wheat germ oil, calendula oil, cherry kernel oil, cucumber seed oil, papaya oil, aloe vera oil, hemp oil, safflower oil, or a combination of any two or more thereof. The saponification values are shown in Table 1 below.

TABLE 1

| OIL | SAP |
| --- | --- |
| Almond oil | 185-200 |
| Apricot oil | 185-195 |
| Argan oil | 185-200 |
| Avocado | 177-196 |
| Babassu oil | 245-256 |
| Blackcurrant oil | 185-195 |
| Brazil nut oil | 245-256 |
| Camelina oil | 185-197 |
| Camellia oil | 185-197 |
| Canola oil | 188-198 |
| Castor oil | 175-187 |
| Cocoa oil | 173-188 |
| Coconut oil | 245-265 |
| Copaiba oil | 140 |
| Flaxseed oil | 188-196 |
| Grapeseed oil | 185-200 |
| Hazelnut oil | 180-200 |
| Hemp | 190-195 |
| Marula oil | 188-196 |
| Moringa oil | 193 |
| Neem oil | 175-205 |
| Olive | 184-196 |
| Palm oil | 190-205 |
| Plum oil | 170-210 |
| Pumpkin seed oil | 187-195 |
| Red raspberry | 184-191 |
| Safflower | 185-198 |
| Sesame oil | 186-199 |
| Shea oil | 170-195 |
| Soybean oil | 190 |
| Sunflower oil | 185-195 |
| Walnut oil | 190-197 |
| Wheat germ oil | 180-200 |

In certain embodiments, the at least one plant oil comprises at least one oil chosen from sunflower oil, high oleic sunflower oil, coconut oil, hemp oil, avocado oil, olive oil, sesame oil, shea oil, safflower oil, argan oil, raspberry oil, or a combination of any two or more thereof.

In certain embodiments, the at least one plant oil has a melting point of −25° C. to 30° C.

In certain embodiments, the at least one plant oil comprises a plant oil which has a saponification value of 150 to 200 mg KOH/g.

In certain embodiments, the at least one plant oil is a plant oil which has a saponification value of 170 to 200 mg KOH/g.

In certain embodiments, the plant oil is sunflower oil, optionally high oleic sunflower oil.

In certain embodiments, the at least one plant oil is a combination of a first oil and a second oil, the first oil having a saponification value of 150 to 200 mg KOH/g and the second oil having a saponification value of 220 to 275 mg KOH/g.

In certain embodiments, the first oil is present at a concentration of 10 to 20 weight %, based on the total weight of the composition, and the second oil is present at a concentration of 1 to 10 weight %, based on the total weight of the composition.

In certain embodiments, the first oil is present at a concentration of 12 to 14 weight %, based on the total weight of the composition, and the second oil is present at a concentration of 3 to 7 weight %, based on the total weight of the composition.

In certain embodiments, the first oil has a melting point of −18° C. to −5° C. and the second oil has a melting point of 10° C. to 25° C.

In certain embodiments, the first oil is sunflower oil and the second oil is coconut oil.

In certain embodiments, the composition further comprises a vegetable fat having a melting point of 31° C. to 60° C.

In certain embodiments, the vegetable fat is at least one material chosen from cocoa butter, shea butter, palm butter, tucuma butter, avocado butter, kokum butter, olive butter, shorea butter, manoi butter, coffee butter, soy butter, jojoba butter, cupuacu butter, mango butter, pistachio butter, pumpkin seed butter, brazil nut butter, hemp seed butter, illipe butter, murumuru butter, ucuuba butter, and combinations thereof.

In certain embodiments, the vegetable fat is present in a concentration of 1 to 10 weight %, based on the total weight of the composition.

In some embodiments, the at least one ester is propylene glycol dicaprate. In some embodiments, the at least one ester is 1,3-propanediol dicaprylate. In some embodiments, the at least one ester is glyceryl dilaurate. In some embodiments, the at least one ester is acetylated glycol stearate. In some embodiments, the at least one ester is tricaprylin (caprylic triglyceride). In some embodiments, the at least one ester is tricaprin (capric triglyceride). In some embodiments, the at least one ester is PEG-6 caprylic/capric glycerides (such as Glycerox™ 767HC from Croda). In some embodiments, the at least one ester is cocoglycerides (a mixture of mono-, di- and tri-glycerides derived from coconut oil). In some embodiments, the at least one ester is glycerol caprylate caprate (which is a mixture of capric monoglycerides and caprylic monoglycerides). In some embodiments, the at least one ester is caprylic/capric/stearic triglyceride.

The composition may also further comprise one or more ingredients selected from vitamins, fatty alcohols, starches, silicas, essential oils, colorants, titanium dioxide, zinc oxide and mixtures of any two or more thereof. An example of a suitable vitamin is vitamin E (tocopherol acetate). An example of a suitable fatty alcohol is cetyl alcohol. Examples of silicas include thickening silica. Examples of essential oils which may be used as natural fragrances include lavender oil, apricot oil, bay oil, calendula oil, Aztec marigold oil, lemongrass oil, rose oil, lime oil, white grapefruit oil. Further fragrances which may be used include natural lavender vanilla fragrance.

In some embodiments, the composition comprises zinc oxide. In certain embodiments, the zinc oxide is non-nano zinc oxide, i.e. the zinc oxide has an average particle size of greater than 100 nm. Furthermore, in such embodiments, the zinc oxide is added to the compositions as a powder, not as a pre-formed dispersion of zinc oxide in a carrier. In some embodiments, the zinc oxide may be present in the composition in a concentration of 10 to 30 weight %, from 15 to 25 weight %, from 18 to 23 weight %, or about 20 weight %, based on the total weight of the composition.

In some embodiments, the zinc oxide may be present in a concentration of 10 to 20 weight %, from 11 to 15 weight %, or about 12 weight %, based on the total weight of the composition.

In some embodiments, the composition comprises: (i) 50 to 60 weight % of a combination of caprylic triglyceride and capric triglyceride, wherein the weight ratio of caprylic triglyceride to capric triglyceride is about 60:40; (ii) 13.5 to 15 weight % beeswax; (iii) 1 to 3 weight % hydrogenated castor oil (e.g, CastorWax MP80); (iv) 10 to 12.5 weight % sunflower oil; and (v) 10 to 22 weight % zinc oxide. The composition can alternatively consist of these materials. The composition can be a sunscreen or a diaper cream.

In some embodiments, the composition comprises or consists of 20 weight % zinc oxide, 10 weight % sunflower oil, 53 weight % caprylic/capric triglyceride, 15 weight % beeswax, and 2 weight % hydrogenated castor oil.

In certain embodiments, the composition comprises or consists of 20 weight % zinc oxide, 12.5 weight % sunflower oil, 52 weight % caprylic/capric triglyceride, 13.5 weight % beeswax, and 2 weight % hydrogenated castor oil.

In certain embodiments, the composition comprises or consists of 20 weight % zinc oxide, 12.1 weight % sunflower oil, 52 weight % caprylic/capric triglyceride, 13.5 weight % beeswax, 2 weight % hydrogenated castor oil, and 0.4 weight % fragrance.

In certain embodiments, the composition comprises or consists of 12 weight % zinc oxide, 12.5 weight % sunflower oil, 60 weight % caprylic/capric triglyceride, 13.5 weight % beeswax, and 2 weight % hydrogenated castor oil.

In certain embodiments, the composition comprises or consists of 12 weight % zinc oxide, 12.5 weight % sunflower oil, 55 weight % caprylic/capric triglyceride, 13.5 weight % beeswax, 5 weight % shea butter, and 2 weight % hydrogenated castor oil.

In certain embodiments, the composition comprises or consists of 12 weight % zinc oxide, 12.5 weight % sunflower oil, 55 weight % caprylic/capric triglyceride, 13.5 weight % beeswax, 5 weight % coconut oil, and 2 weight % hydrogenated castor oil.

In certain embodiments, the composition comprises or consists of 12 weight % zinc oxide, 12.5 weight % sunflower oil, 60 weight % caprylic/capric triglyceride, 13.5 weight % beeswax, and 2 weight % hydrogenated castor oil.

In certain embodiments, the composition comprises or consists of 12 weight % zinc oxide, 12.5 weight % sunflower oil, 52 weight % caprylic/capric triglyceride, 13.5 weight % beeswax, 5 weight % coconut oil, 3 weight % shea butter, and 2 weight % hydrogenated castor oil.

In certain embodiments, the composition comprises or consists of 20 weight % zinc oxide, 10.4 weight % sunflower oil, 48% caprylic/capric triglyceride, 13.5% beeswax, 5 weight % sunflower seed wax, 3 weight % hydrogenated castor oil, and 0.1 weight % oil.

In certain embodiments, the composition comprises or consists of 20 weight % zinc oxide, 7.4 weight % sunflower oil, 51% caprylic/capric triglyceride, 13.5% beeswax, 5 weight % sunflower seed wax, 3 weight % hydrogenated castor oil, and 0.1 weight % oil.

The composition can also be a stick. In certain embodiments, the stick comprises 46 to 56% by weight of the ester, 8 to 19% by weight of the first wax, 3 to 15% by weight of the second wax, and 5 to 12% of the plant oil. In other embodiments, the stick comprises 47 to 53% by weight of the ester, 11 to 16% by weight of the first wax, 6 to 10% by weight of the second wax, and 6 to 11% of the plant oil.

In certain embodiments, the second wax in the stick comprises sunflower seed wax. Optionally, the second wax can further include hydrogenated castor oil. In certain embodiments, a weight ratio of sunflower seed wax to hydrogenated castor oil is 1.5 to 1.8 or about 1.67. In certain embodiments for the stick, the ester comprises caprylic/capric triglyceride, the first wax comprises beeswax, and the plant oil comprises sunflower seed oil.

In certain embodiments, the stick can have a hardness of 300 to 550 g. In other embodiments, the hardness is 400 to 500 g. In certain embodiments, the stick can have a melt point of 52 to 65° C. In other embodiments, the melt point is 59 to 63° C. or 61 to 62° C. The stick can have low barrel adhesion when dispensed from a stick barrel (as seen by a smooth surface on the stick). The stick can also provide less whitening when applied to skin. In one embodiment, the lotions/creams can be made into a stick by the addition of sunflower seed wax. In certain embodiments, the stick compositions are filled into containers at 55 to 70° C. or 65 to 70° C.

The melt point is measured by Differential Scanning calorimetry (DSC, e.g., using a TA Instruments Model Q20. A sample of known weight is placed into the instrument and equilibrated at 25° C. and held for one minute. Data recording is started, and the temperature is ramped at 2° C./minute to 100° C. and held isothermal for one minute. This is the end of cycle 1. The temperature is then ramped at 2° C./minute to 0° C. and held isothermal for one minute. This is the end of cycle 2. The temperature is then ramped at 2° C./minute to 100° C. This is the end of cycle 3. The data sampling interval is 0.2 seconds.

The hardness is the absolute peak downstroke force that occurs during initial compression with a probe, e.g., measured using a TA Instruments XT Plus Stable Microsystems Texture Analyzer. The texture analyzer is equipped with a 45° Cone Perspex probe and run in compression mode at room temperature (23-25° C.). The force is set at 100.0 g, speed at 1.00 mm/second, and distance at 5.0 mm. The stick sample is placed on platform and 3 measurements are taken on the sample face and averaged. The hardness measurement is reported in grams.

The composition can also be an antiperspirant or lip balm. In certain embodiments, the composition is not an antiperspirant or a lip balm.

The composition can be a sunscreen or a diaper cream.

In any of the above-described embodiments, the compositions may be formulated from all-natural ingredients, i.e. consist of natural ingredients.

EXAMPLES

Example 1

Various sunscreen compositions were formulated, in which the concentrations of caprylic/capric triglyceride, sunflower oil, beeswax and hydrogenated castor oil were varied. Some of these compositions also contained shea butter, tapioca starch, cetyl alcohol or thickener silica.

These compositions were prepared as follows:
1. The beeswax, hydrogenated castor oil (CastorWax MP 80), sunflower oil, and triglyceride were combined in a suitable container. If used, the cetyl alcohol, shea butter, or Natural Jelly SP511 were also added to the mixture in this step.
2. The mixture was heated to 80° C. to melt the waxes, with mixing during heating to maintain uniformity (using a bench-top IWK RW16 basic lightening mixer and an axial blade propeller, with mixing speed dial set at 4).
3. When the waxes had melted and the mixture was clear (homogeneous/uniform), zinc oxide was added and the mixing was continued for 10 minutes while maintaining the temperature at 80° C. (with the mixing speed dial set at 4-5).
4. After 10 minutes mixing on the bench-top mixer, the mixture was homogenized at 5000 RPM for 10 minutes using a Silverson L4RT bench-top homogenizer.
5. The mixture was removed from the Silverson homogenizer after 10 minutes and moved back to the IWK lightening mixer.
6. As the mixture cooled and thickened, the mixing speed dial was adjusted, starting with dial setting 4-5 and then increasing to 7-8.

7. Mixing was continued while cooling to 25-28° C. If used, the silica or starch were added during cooling when the mixture reached a temperature of 50 to 55° C.
8. The mixture was then filled into the desired container.

The freeze-thaw stability of the compositions was also investigated. The freeze temperature was −10° C., and the thaw temperature was 25° C. (at 60% relative humidity). The cycle of freezing and thawing (i.e. 24 hours of freezing followed by 24 hours of thawing) was repeated three times for each sample tested. Samples which failed this test had separated into two bulk phases. The viscosity of the compositions was also measured after they had been subjected to the three cycles of freezing and thawing.

The physical stability of each composition at 49° C. was also investigated (with a "fail" indicating separation into two bulk phases).

An assessment of the amount of white residue left on the skin following application was also carried out (indicated as "whitening acceptability" in Table 2).

The dispensing acceptability of the compositions was also assessed.

The greasiness and afterfeel acceptability of the compositions was also assessed.

Sunscreen compositions containing various amounts of caprylic/capric triglyceride, sunflower oil and waxes are shown in Table 2.

TABLE 2

Sunscreens.

| | 1* | 2* | 3* | 4* | 5* | 6* | 7* | 8 | 9* | 10* | 11 |
|---|---|---|---|---|---|---|---|---|---|---|---|
| | Weight % | | | | | | | | | | |
| Zinc Oxide | 20 | 20 | 20 | 20 | 20 | 20 | 20 | 20 | 20 | 20 | 20 |
| Sunflower oil | 57 | 30 | 10 | 10 | 10 | 10 | 10 | 10 | 10 | 10 | 12.5 |
| Caprylic/Capric Triglyceride | 5 | 35 | 55 | 53 | 53 | 54 | 54 | 53 | 53 | 50 | 52 |
| Beeswax | 13 | 15 | 15 | 17 | 17 | 15 | 15 | 15 | 15 | 15 | 13.5 |
| Shea butter | 5 | 0 | 0 | 0 | 0 | 0 | 0 | 0 | 0 | 0 | 0 |
| CastorWax MP80 hydrogenated castor oil | 0 | 0 | 0 | 0 | 0 | 0 | 0 | 2 | 0 | 0 | 2 |
| Tapioca starch | 0 | 0 | 0 | 0 | 0 | 0 | 1 | 0 | 0 | 0 | 0 |
| Cetyl Alcohol | 0 | 0 | 0 | 0 | 0 | 0 | 0 | 0 | 2 | 0 | 0 |
| Thickener silica | 0 | 0 | 0 | 0 | 0 | 1 | 0 | 0 | 0 | 0 | 0 |
| Natural jelly SP511 | 0 | 0 | 0 | 0 | 0 | 0 | 0 | 0 | 0 | 5 | 0 |
| Total | 100 | 100 | 100 | 100 | 100 | 100 | 100 | 100 | 100 | 100 | 100 |
| Freeze/thaw stability | F/T 3 Pass | F/T 3 Pass | F/T 3 Pass | F/T 3 Pass | F/T 3 Pass | F/T 3 Pass | F/T 3 Pass | F/T 3 Pass | F/T 3 Pass | F/T 3 Pass | F/T 3 Pass |
| High temp. stability (49° C.) | Fail | Fail | Fail | Fail | Fail | Fail | Fail | Pass | Fail | Fail | Pass |
| "Whitening" acceptability | No | No | Yes | Yes | Yes | No | No | Yes | No | No | Yes |
| Dispensing acceptability | No | No | No | No | No | No | No | Yes | No | No | Yes |
| Greasiness/afterfeel acceptability | No | No | Yes | Yes | Yes | Yes | Yes | Yes | Yes | No | Yes |

*denotes comparative composition.

As can be seen from Table 2, only Compositions 8 and 11 were able to meet each of the tests. Other compositions, such as 6 or 7, in which additional materials are added to achieve acceptable results for some of the other tests did not provide a composition that was able to meet all five tests.

Example 2

The water activity of two sunscreen compositions was also measured using USP method <1112>. As discussed in this test method, formulas having a water activity of less than 0.6 do not support microbial growth.

The water activity of the two sunscreen compositions tested are shown in Table 3, below:

TABLE 3

Water activity of sunscreen compositions

| Composition# | 11 (weight %) | 12 (weight %) |
|---|---|---|
| Zinc Oxide | 20 | 20 |
| Sunflower oil | 12.5 | 12.1 |
| Caprylic/Capric Triglyceride | 52 | 52 |
| Beeswax | 13.5 | 13.5 |
| CastorWax MP80 hydrogenated castor oil | 2 | 2 |
| Fragrance (natural lavender vanilla fragrance) | 0 | 0.40 |
| Total | 100 | 100 |

TABLE 3-continued

Water activity of sunscreen compositions

| Composition# | 11 (weight %) | 12 (weight %) |
|---|---|---|
| | Water activity | |
| Sample #1 | 0.262 | 0.306 |
| Sample #2 | 0.265 | 0.309 |
| Sample #3 | 0.268 | 0.304 |

As can be seen from the above water activity results, the sunscreens do not support microbial growth.

Example 3

The Sun Protection Factor (SPF) of Composition #12 (formula as in Table 3, above) was tested on human skin using the procedure defined by the FDA Sunscreen Final Rule; CFR Parts 201 and 310 [Docket No. FDA-1978-N-0018] (formerly Docket No. 1978N-0038), RIN 0910-AF43, Labeling and Effectiveness Testing; Sunscreen Drug Products For Over-The-Counter Human Use [FR Doc. 2011-14766 Filed 16 Jun. 2011; Publication Date 17 Jun. 2011] using a xenon arc solar simulator as the UV source. This test was conducted prior to and immediately following an 80 minute water immersion experiment which was carried out under controlled conditions as described in the above-mentioned FDA Sunscreen Final Rule.

When tested on ten subjects, Composition #12 yielded a mean SPF value of 36.03 (label SPF 34) prior to water immersion, and a mean SPF value of 35.01 (label SPF 34) following the 80 minute water immersion experiment.

It was further noted that Composition #12 of the present invention achieved 80 minutes of water resistance according to the test defined in 21 CFR 352.76, whereas each of the comparative commercial sunscreens as listed in Table 4, below (each of which were SPF 30), only achieved 40 minutes of water resistance.

TABLE 4

Comparative commercial sunscreens with label ingredients

| Commercial I | Commercial II | Commercial III | Commercial IV | Commercial V |
|---|---|---|---|---|
| Zinc oxide 18.75 weight % | Zinc oxide 18.75 weight % | Zinc oxide 18.75 weight % | Zinc oxide 18.75 weight % | Zinc oxide 20 weight % |
| Sunflower oil | Sunflower oil | Sunflower oil | Olive oil | Sunflower oil |
| Beeswax | Beeswax | Beeswax | Beeswax | Beeswax |
| Seabuckthorn extract | Sweet orange essential oil | Seabuckthorn extract | Jojoba oil | Caprylic/capric triglyceride |
| Calendula extract | Tangerine essential oil | Tocopherol vitamin E | Shea butter | Polyhydroxystearic acid |
| Chamomile essential oil | Seabuckthorn extract | | Cocoa butter | Calendula flower extract |
| Tocopherol Vitamin E | Vanilla extract | | Lavender essential oil | Matricaria flower extract |
| | Tocopherol Vitamin E | | Tocopherol Vitamin E | Olive fruit oil |
| | | | Seabuckthorn extract | triethoxycaprylylsilane |
| | | | | Shea butter |

Example 4

Various diaper creams were also formulated, each of which contained 12 weight % zinc oxide, 13.5 weight % beeswax and 2 weight % hydrogenated castor oil. These formulations are shown in Table 5, below.

TABLE 5

Diaper cream formulations

| | Composition# | | | | | |
|---|---|---|---|---|---|---|
| | A | B | C | D | E | F |
| | Weight % | | | | | |
| Zinc Oxide | 12 | 12 | 12 | 12 | 12 | 12 |
| Sunflower oil | 12.5 | 12.5 | 12.5 | 12.5 | 12.49 | 20.49 |
| Caprylic/Capric Triglyceride | 60 | 55 | 55 | 52 | 52 | 52 |
| Coconut oil | 0 | 0 | 5 | 5 | 5 | 0 |
| Beeswax | 13.5 | 13.5 | 13.5 | 13.5 | 13.5 | 13.5 |
| Shea butter | 0 | 5 | 0 | 3 | 3 | 0 |
| CastorWax MP80 hydrogenated castor oil | 2 | 2 | 2 | 2 | 2 | 2 |
| Vitamin E | 0 | 0 | 0 | 0 | 0.01 | 0.01 |
| Total | 100 | 100 | 100 | 100 | 100 | 100 |

Each of these diaper creams contained the combination of beeswax and hydrogenated castor oil which was also present in sunscreen Composition 11.

Example 5

Composition 11 was compared against Commercial 1 for gloss after application to skin by 11 trained sensory panelists. The panelists assigned a score of 0 to 100 with 0=dull/flat to 100=shiny/glossy. The results of the panelists are averaged. The results are shown in Table 6 below.

TABLE 6

| | Gloss | |
|---|---|---|
| Application Time | 11 | Commercial 1 |
| Immediately after rub in | 37.1 | 41.3 |
| 20 minutes after rub in | 23.6 | 26.0 |

As can be seen, the inventive composition 11 has a lower gloss as compared to Commercial 1 immediately and 20 minutes after application. This indicates that the composition is less greasy because there is less reflected light on the surface of the skin to create gloss.

Example 6

The composition can be formed into a stick product, such as a sunscreen stick, by the addition of sunflower seed wax, prepared as follows, and filled into a dispensing barrel. The formulation is provided in Table 7 below.

TABLE 7

| Sunscreen Stick Formulation | |
|---|---|
| Material | Weight % |
| Caprylic/capric triglyceride | 51 |
| Zinc oxide | 20 |
| Beeswax | 13.5 |
| Sunflower seed oil | 7.4 |
| Sunflower seed wax | 5 |
| Hydrogenated castor oil (Castor Wax MP80) | 3 |
| Vitamin E Acetate | 0.1 |

The beeswax, the hydrogenated castor oil, sunflower seed wax, sunflower oil, and triglyceride are combined and heated to 80° C. to melt the waxes with mixing using an IWK RW16 basic lightening mixer and axial blade propeller with mixing speed dial set at 4. After the waxes melted, zinc oxide is added and mixed for 10 minutes while maintaining the temperature at 80° C. and the mixer at the same speed. The mixture is homogenized at 5000 rpm using a Silverson L4RT homogenizer for 10 minutes. The mixture is transferred back to the lightening mixer and mixed for 10 minutes with a speed dial setting of 4-5. The mixture is cooled to 70° C. while mixing is continued. Vitamin E acetate is added and mixed for 10 minutes at the same speed setting. The mixture is cooled to 65-70° C. and then filled into a barrel stick container.

The stick had a desired hardness (432 g) and melt point (61.3° C.) for a stick suitable for dispensing from a barrel. The combination of materials provided low barrel adhesion when dispensed. The composition also appeared to have less whitening when applied to skin.

What is claimed is:

1. An anhydrous personal care composition, comprising:
   (a) at least one ester, wherein said at least one ester is selected from one or more of the following groups:
      (i) triglycerides,
      (ii) diglycerides,
      (iii) monoglycerides,
      (iv) monoesters of diols, and
      (v) diesters of diols,
      and wherein a total concentration of said at least one ester is 45 to 60 weight %, based on the total weight of the composition;
   (b) a first wax having a melting point of 35° C. to 72° C. present in an amount of 5 to 25 weight %, based on the total weight of the composition;
   (c) a second wax having a melting point of 73° C. to 90° C. present in an amount of 0.5 to 15 weight % based on the total weight of the composition; and
   (d) at least one plant oil having a saponification value of 150 to 275 mg KOH/g, wherein a total concentration of said at least one plant oil is from 5 to 35 weight %, based on the total weight of the composition.

2. The composition of claim 1, which is a stick that comprises
   a. 46 to 56% by weight of the ester,
   b. 8 to 19% by weight of the first wax,
   c. 3 to 15% by weight of the second wax, and
   d. 5 to 12% of the plant oil.

3. The composition of claim 1, which is a stick that comprises
   a. 47 to 53% by weight of the ester,
   b. 11 to 16% by weight of the first wax,
   c. 6 to 10% by weight of the second wax, and
   d. 6 to 11% of the plant oil.

4. The composition of claim 1, wherein the second wax comprises sunflower seed wax.

5. The composition of claim 4, wherein the second wax further comprises hydrogenated castor oil.

6. The composition of claim 5, wherein a weight ratio of sunflower seed wax to hydrogenated castor oil is 1.5 to 1.8 or about 1.67.

7. The composition of claim 1, wherein the ester comprises caprylic/capric triglyceride, the first wax comprises beeswax, and the plant oil comprises sunflower seed oil.

8. The composition of claim 1, which is a stick that has a melt temperature of 52 to 65° C.

9. The composition of claim 8, wherein the stick has a melt temperature of 59 to 63° C. or 61 to 62° C.

10. The composition of claim 1, which is a stick that has a hardness of 300 to 550 g.

11. The composition of claim 10, wherein the stick has a hardness of 400 to 500 g.

12. The composition of claim 1, wherein the composition is not an antiperspirant or a lip balm.

13. The composition of claim 1, wherein the composition is a sunscreen.

14. The composition of claim 13, wherein the composition comprises a sun-protective level of zinc oxide particles.

15. The composition of claim 1, wherein the composition is a diaper cream.

16. The composition of claim 1 wherein elements (a), (b), (c), and (d) of claim 1 are separate components which are combined to provide the composition.

17. The composition of claim 1 which is substantially homogenous at room temperature and which does not undergo separation when stored at a temperature of 49° C. for 13 weeks.

18. A method of making the composition of claim 1 comprising
   a. combining the ester, the first wax, the second wax, and the plant oil,
   b. heating the ester, the first wax, the second wax, and the plant oil to a temperature at or above a melting point of all of the ester, the first wax, the second wax, and the plant oil,
   c. mixing the ester, the first wax, the second wax, and the plant oil to form a mixture, and
   d. filling the mixture into a container, wherein a temperature of the mixture is 55 to 70° C.

19. The method of claim 18, wherein the temperature of the mixture at filling is 65 to 70° C.

20. A method of reducing the risk of sun damage to the skin comprising applying a composition according to claim 13 to the skin.

* * * * *